United States Patent
Negishi et al.

(10) Patent No.: US 9,507,139 B2
(45) Date of Patent: Nov. 29, 2016

(54) SPECIMEN HOLDER, SPECIMEN PREPARATION DEVICE, AND POSITIONING METHOD

(71) Applicant: JEOL Ltd., Tokyo (JP)

(72) Inventors: Tsutomu Negishi, Tokyo (JP); Tooru Kasai, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 14/944,517

(22) Filed: Nov. 18, 2015

(65) Prior Publication Data

US 2016/0139398 A1  May 19, 2016

(30) Foreign Application Priority Data

Nov. 19, 2014 (JP) ................................. 2014-234454

(51) Int. Cl.
```
G01N 1/32      (2006.01)
G02B 21/26     (2006.01)
H01J 37/20     (2006.01)
H01J 37/31     (2006.01)
```
(52) U.S. Cl.
CPC .................. *G02B 21/26* (2013.01); *G01N 1/32* (2013.01); *H01J 37/20* (2013.01); *H01J 2237/20207* (2013.01)

(58) Field of Classification Search
CPC .......... G02B 21/26; H01J 37/20; G01N 1/32
See application file for complete search history.

(56) References Cited

U.S. PATENT DOCUMENTS

| 4,223,257 A | 9/1980 | Miller | |
|---|---|---|---|
| 2005/0118065 A1* | 6/2005 | Hasegawa | H01J 37/28 422/502 |
| 2013/0124325 A1 | 5/2013 | Alvin | |
| 2013/0134325 A1 | 5/2013 | Negishi | |
| 2013/0240353 A1* | 9/2013 | Watanabe | H01J 37/20 204/298.36 |

FOREIGN PATENT DOCUMENTS

JP    2013137995 A    7/2013

OTHER PUBLICATIONS

Extended European Search Report re EP 15194591.2, dated Apr. 13, 2016.

* cited by examiner

*Primary Examiner* — Jack Berman
*Assistant Examiner* — Eliza Osenbaugh-Stewar
(74) *Attorney, Agent, or Firm* — The Webb Law Firm

(57) ABSTRACT

A specimen holder is used for an optical microscope, comprising: a specimen support that supports a specimen to enable the specimen to tilt relative to the optical axis of the optical microscope; an adjustment plate that has an observation surface for making observations using the optical microscope; and an adjustment plate support that supports the adjustment plate, so that the angle formed by the optical axis and the observation surface is larger than the angle formed by the optical axis and a specimen surface of the specimen.

10 Claims, 13 Drawing Sheets

SPECIMEN HOLDER, SPECIMEN PREPARATION DEVICE, AND POSITIONING METHOD

Japanese Patent Application No. 2014-234454 filed on Nov. 19, 2014, is hereby incorporated by reference in its entirety.

BACKGROUND OF THE INVENTION

The present invention relates to a specimen holder, a specimen preparation device, and a positioning method.

A specimen preparation device which utilizes an ion beam (ion beam processing device) is known as a device for preparing an observation-analysis target specimen using an electron microscope, an electron probe microanalyser (EPMA), an Auger microprobe, or the like (see JP-A-2013-137995, for example).

When processing the surface of the specimen by applying an ion beam to the surface of the specimen at an incident angle close to 90° using such a specimen preparation device, the specimen is normally positioned using an optical microscope.

FIG. 21 is a view schematically illustrating the state of a specimen 2, when processing the specimen 2 by applying an ion beam to a specimen surface 4 of the specimen 2 at an incident angle theta close to 90°. Note that the arrow illustrated in FIG. 21 represents an axis which corresponds to the optical axis of the ion beam (or the optical axis of the optical microscope).

Since the depth of focus of an optical microscope is shallow, the in-focus range on the tilted specimen surface 4 illustrated in FIG. 21 is narrow. Therefore, it is difficult to cause the ion beam application position to coincide with the target on the tilted specimen surface 4 using an optical microscope. Thus, the specimen is positioned as described below, for example.

FIGS. 22A to 22D are views illustrating an example of a known specimen positioning method that positions the specimen 2. Note that the intersection of the dash-dotted lines illustrated in FIGS. 22A to 22D represents the axis of tilt of the specimen. The ion beam application position is situated on the axis of tilt.

As illustrated in FIG. 22A, the specimen surface 4 of the specimen 2 is placed perpendicular to the optical axis of the optical microscope, so that the target on the specimen surface 4 can be easily observed using the optical microscope.

As illustrated in FIG. 22B, the position of the specimen 2 is adjusted in the height direction so that the specimen surface 4 coincides with the axis of tilt.

As illustrated in FIG. 22C, the target on the specimen surface 4 is moved to coincide with the ion beam application position using the optical microscope.

As illustrated in FIG. 22D, the specimen 2 is tilted at the tilt angle used when processing the specimen 2 by applying the ion beam. In this case, since the target on the specimen surface 4 is situated on the axis of tilt, the target does not move when the specimen 2 is tilted. Note that the arrow illustrated in FIG. 22D represents the ion beam.

The specimen can be positioned by performing the above steps.

According to the above specimen positioning method, however, it is necessary to cause the specimen surface 4 to coincide with the axis of tilt of the specimen (see FIG. 22B). Therefore, it is necessary to provide a mechanism which accurately adjusts the height of the specimen 2 in the specimen stage. Moreover, even when the target on the specimen surface 4 is moved to coincide with the ion beam application position (see FIG. 22C), the position of the target may be shifted when the specimen 2 is tilted (see FIG. 22D) depending on the accuracy of the specimen tilt mechanism.

Specifically, it is difficult to accurately position the specimen using the above specimen positioning method.

SUMMARY

One aspect of the invention may provide a specimen holder that makes it possible to easily and accurately position a specimen. Another aspect of the invention may provide a specimen preparation device that includes the specimen holder. Another aspect of the invention may provide a positioning method that makes it possible to easily and accurately position a specimen.

According to a first aspect of the invention, there is provided a specimen holder that is used for an optical microscope, comprising:

a specimen support that supports a specimen to enable the specimen to tilt relative to an optical axis of the optical microscope;

an adjustment plate that has an observation surface for making observations using the optical microscope; and an adjustment plate support that supports the adjustment plate so that an angle formed by the optical axis and the observation surface is larger than an angle formed by the optical axis and a specimen surface of the specimen.

According to a second aspect of the invention, there is provided a specimen preparation device including the specimen holder.

According to a third aspect of the invention, there is provided a positioning method that positions a specimen using an optical microscope, the positioning method comprising:

placing an adjustment plate relative to a specimen that is supported to enable a specimen surface to tilt relative to an optical axis of the optical microscope, so that an angle formed by the optical axis and an observation surface of the adjustment plate is larger than an angle formed by the optical axis and the specimen surface; and positioning the specimen while focusing the optical microscope on the adjustment plate.

Figure 1:
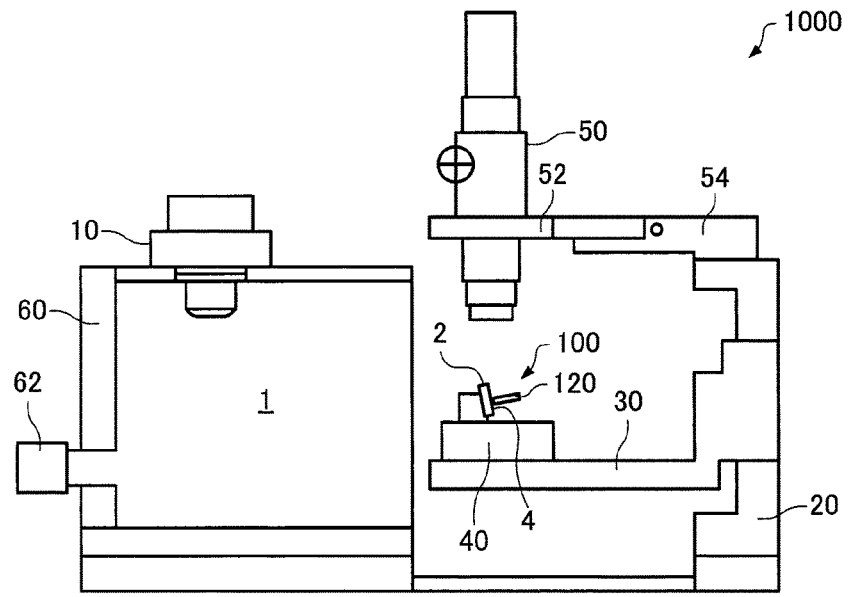
FIG. 1 is a view schematically illustrating the configuration of a specimen preparation device that includes a specimen holder according to one embodiment of the invention.

DETAILED DESCRIPTION OF THE EMBODIMENT (1) According to one embodiment of the invention, a specimen holder that is used for an optical microscope, comprising:

a specimen support that supports a specimen to enable the specimen to tilt relative to an optical axis of the optical microscope;

an adjustment plate that has an observation surface for making observations using the optical microscope; and an adjustment plate support that supports the adjustment plate so that an angle formed by the optical axis and the observation surface is larger than an angle formed by the optical axis and a specimen surface of the specimen.

Since the specimen holder is configured so that the adjustment plate support supports the adjustment plate so that the angle formed by the optical axis of the optical microscope and the observation surface of the adjustment plate is larger than the angle formed by the optical axis of the optical microscope and the specimen surface of the specimen, the optical microscope can be focused on the observation surface of the adjustment plate over a wide range as compared with the specimen surface. It is possible to easily and accurately position the specimen by positioning the specimen while focusing the optical microscope on the adjustment plate.

Since the specimen holder is configured in such a way that the specimen can be positioned while focusing the optical microscope on the adjustment plate, the specimen can be positioned while the specimen surface is tilted. Therefore, it is possible to more accurately position the specimen, as compared with the case in which the specimen is tilted after the specimen has been positioned while the specimen surface is perpendicular to the optical axis of the optical microscope, for example.

(2) In the specimen holder, a marker that serves as a mark used when positioning the specimen may be formed on the observation surface.

Since the specimen holder is configured so that the specimen can be positioned using the optical microscope utilizing the marker as a mark, it is possible to more accurately position the specimen.

(3) In the specimen holder, the adjustment plate can be movable so that the distance from the specimen surface can be changed.

This makes it possible to bring the adjustment plate into contact with the specimen (or bring the adjustment plate closer to the specimen) independently of the thickness of the specimen and the convexities and concavities of the specimen surface, for example. Therefore, the adjustment plate (marker) can be brought into contact with the target on the specimen surface (or brought closer to the target on the specimen surface), and it is possible to more accurately position the specimen.

(4) In the specimen holder, the marker may include a part that extends from an edge of the adjustment plate in a diagonal direction.

This makes it possible to clearly determine the boundary between the adjustment plate and the specimen even when the observation surface of the adjustment plate is reflected on the specimen surface when positioning the specimen using the optical microscope. Therefore, it is possible to easily and accurately position the specimen using the optical microscope.

(5) In the specimen holder, the adjustment plate support may support the adjustment plate so that the adjustment plate is tilted when the specimen is tilted by the specimen support.

This makes it possible to set the angle formed by the specimen surface and the observation surface of the adjustment plate to be constant independently of the tilt angle of the specimen.

(6) In the specimen holder, the angle formed by the specimen surface and the observation surface may be 90°.

According to this configuration, the angle formed by the observation surface of the adjustment plate and the optical axis of the optical microscope can be set to be close to 90° when processing the specimen surface by applying an ion beam to the specimen surface at an incident angle close to 90°. Therefore, the optical microscope can be focused on the observation surface of the adjustment plate over a wide range. This makes it possible to easily and accurately position the specimen using the optical microscope.

(7) According to another embodiment of the invention, a specimen preparation device includes the specimen holder.

Since the specimen preparation device includes the specimen holder, it is possible to easily and accurately position the specimen.

(8) The specimen preparation device may further include an ion source that generates an ion beam, and may apply the ion beam to the specimen to process the specimen.

This makes it possible to easily and accurately process the desired position of the specimen using the specimen preparation device.

(9) According to another embodiment of the invention, a positioning method that positions a specimen using an optical microscope, the positioning method comprising:

placing an adjustment plate relative to a specimen that is supported to enable a specimen surface to tilt relative to an optical axis of the optical microscope, so that an angle formed by the optical axis and an observation surface of the adjustment plate is larger than an angle formed by the optical axis and the specimen surface; and positioning the specimen while focusing the optical microscope on the adjustment plate.

According to the positioning method, since the adjustment plate is placed in such a way that the angle formed by the optical axis of the optical microscope and the observation surface of the adjustment plate is larger than the angle formed by the optical axis of the optical microscope and the specimen surface of the specimen, the optical microscope can be focused on the observation surface of the adjustment plate over a wide range as compared with the specimen surface. It is possible to easily and accurately position the specimen by positioning the specimen while focusing the optical microscope on the adjustment plate.

Furthermore, according to the positioning method since the specimen can be positioned while focusing the optical microscope on the adjustment plate, the specimen can be positioned while the specimen surface is tilted. Therefore, it is possible to more accurately position the specimen, as compared with the case in which the specimen is tilted after the specimen has been positioned while the specimen surface is perpendicular to the optical axis of the optical microscope, for example.

(10) In the positioning method, a marker that serves as a mark used when positioning the specimen may be formed on the observation surface.

According to this configuration, since the marker is formed on the observation surface of the adjustment plate, it is possible to more accurately position the specimen.

Exemplary embodiments of the invention are described in detail below with reference to the drawings. Note that the following exemplary embodiments do not unduly limit the scope of the invention as stated in the claims. Note also that all of the elements described below should not necessarily be taken as essential elements of the invention.

1. Specimen Holder and Specimen Preparation Device

Figure 2:
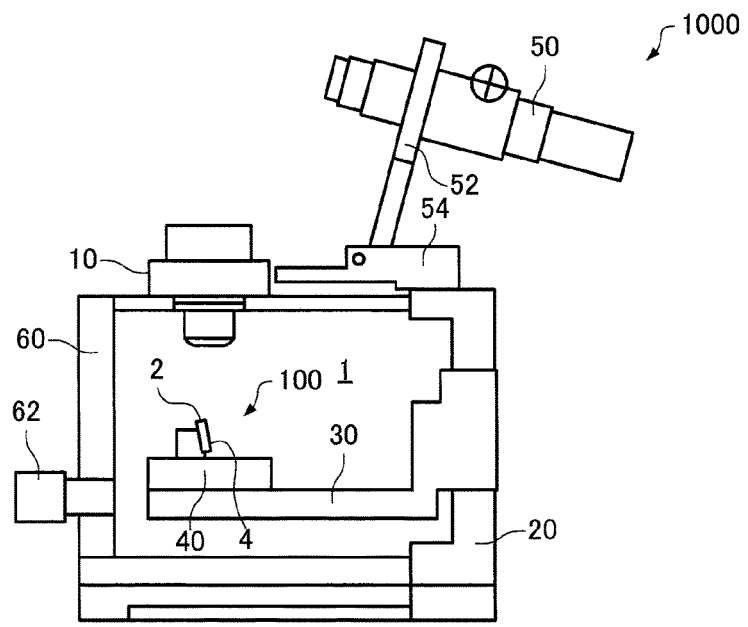
FIG. 2 is a view schematically illustrating the configuration of a specimen preparation device that includes a specimen holder according to one embodiment of the invention.

A specimen holder and a specimen preparation device according to one embodiment of the invention are described below with reference to the drawings. FIGS. 1 and 2 are views schematically illustrating the configuration of a specimen preparation device 1000 that includes a specimen holder 100.

The specimen preparation device 1000 is an ion beam processing device that processes a specimen 2 by applying an ion beam to prepare an observation-analysis target specimen. The specimen preparation device 1000 can prepare an observation-analysis target specimen using a scanning electron microscope (SEM), a transmission electron microscope (TEM), an electron probe microanalyser (EPMA), an Auger microprobe, or the like, for example.

As illustrated in FIGS. 1 and 2, the specimen preparation device 1000 includes the specimen holder 100. Note that the specimen holder 100 is illustrated in FIGS. 1 and 2 in a simplified manner for convenience of illustration.

The specimen preparation device 1000 further includes an ion source 10, a specimen stage unloading mechanism 20, a specimen stage 30, a specimen position adjustment mechanism 40, an optical microscope 50, an optical microscope position adjustment mechanism 52, an optical microscope tilt mechanism 54, a vacuum chamber 60, and a gas discharge device 62. Note that FIG. 1 illustrates a state in which the specimen stage unloading mechanism 20 is opened, and FIG. 2 illustrates a state in which the specimen stage unloading mechanism 20 is closed.

The ion source 10 generates an ion beam. The ion source 10 is provided at the upper part of the vacuum chamber 60. The ion source 10 is an ion gun, for example. The ion source 10 emits the ion beam that is accelerated at a given accelerating voltage. An Ar ion beam may be used as the ion beam, for example. The diameter of the ion beam is about several hundreds of micrometers, for example.

The specimen stage unloading mechanism 20 is provided at the vacuum chamber 60 so as to be openable and closable. The specimen stage 30 is attached to the specimen stage unloading mechanism 20. The specimen stage 30 can be unloaded from a processing chamber 1 by opening the specimen stage unloading mechanism 20 (see FIG. 1). The specimen stage 30 can be loaded into the processing chamber 1 by closing the specimen stage unloading mechanism 20 (see FIG. 2). The processing chamber 1 is evacuated by operating the gas discharge device 62 while the specimen stage unloading mechanism 20 is closed. The processing chamber 1 can thus be set to a vacuum state (decompressed state).

The specimen position adjustment mechanism 40 is provided at the specimen stage 30. The specimen holder 100 that holds the specimen 2 is fitted to the specimen position adjustment mechanism 40. The specimen holder 100 is removable from the specimen position adjustment mechanism 40. The specimen position adjustment mechanism 40 can two-dimensionally move the specimen holder 100 in the horizontal direction. The specimen 2 can be positioned by two-dimensionally moving the specimen 2 in the horizontal direction.

The optical microscope 50 is attached to the upper end of the specimen stage unloading mechanism 20 through the optical microscope position adjustment mechanism 52 and the optical microscope tilt mechanism 54. The specimen 2 can be positioned using the optical microscope 50. Note that the positioning of the specimen 2 in the specimen preparation device 1000 means to adjust the position of the target (or the target area) on a specimen surface 4 (i.e., the surface of the specimen 2) of the specimen 2 to coincide with the application position of the ion beam.

In the specimen preparation device 1000, the optical axis of the optical microscope 50 when the specimen stage unloading mechanism 20 is opened (see FIG. 1) coincides with the optical axis of the ion beam emitted from the ion source 10 when the specimen stage unloading mechanism 20 is closed (see FIG. 2). The specimen preparation device 1000 can adjust the position of the target of the specimen 2 to coincide with the application position of the ion beam, by positioning the target of the specimen 2 at the center of the field of view of the optical microscope 50, for example.

As illustrated in FIGS. 1 and 2, the optical microscope position adjustment mechanism 52 holds the optical microscope 50. The optical microscope position adjustment mechanism 52 is attached to the optical microscope tilt mechanism 54 so as to be tiltable. As illustrated in FIG. 2, the optical microscope 50 and the optical microscope position adjustment mechanism 52 are situated outside the vacuum chamber 60, when the specimen stage unloading mechanism 20 is closed.

Figure 3:
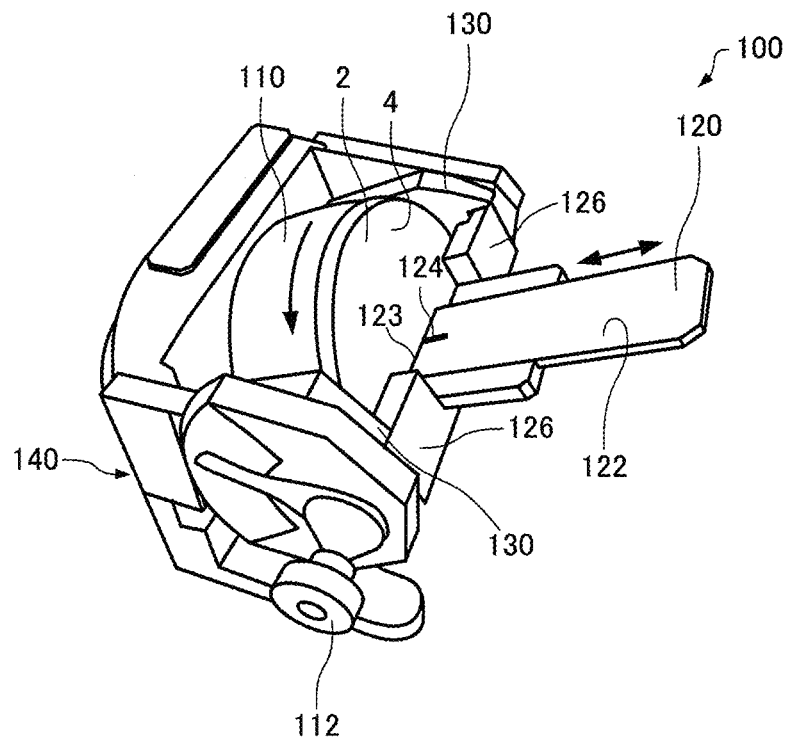
FIG. 3 is a perspective view schematically illustrating a specimen holder according to one embodiment of the invention.
Figure 4:
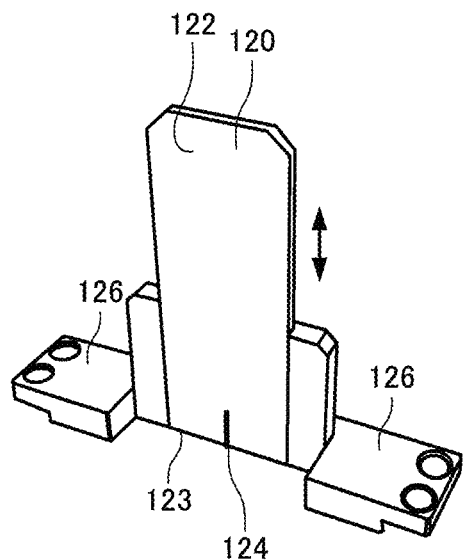
FIG. 4 is a perspective view schematically illustrating an adjustment plate included in a specimen holder according to one embodiment of the invention.

The specimen holder 100 is described below. FIG. 3 is a perspective view schematically illustrating the specimen holder 100. FIG. 4 is a perspective view schematically illustrating an adjustment plate 120 included in the specimen holder 100.

As illustrated in FIG. 3, the specimen holder 100 includes a specimen support 110, the adjustment plate 120, an adjustment plate support 130, and a support stage 140. The specimen holder 100 is an optical microscope specimen holder that is used when observing the specimen 2 using the optical microscope 50. The specimen preparation device 1000 also utilizes the specimen holder 100 when processing the specimen 2 using the ion beam.

The specimen support 110 supports the specimen 2. The specimen support 110 supports the specimen 2 so that the specimen 2 can be tilted. Specifically, when a specimen tilt knob 112 is rotated, the specimen support 110 rotates around the axis of the specimen tilt knob 112 so that the specimen 2 is rotated (tilted). Since the specimen support 110 supports the specimen 2 so that the specimen 2 can be tilted, the specimen 2 can be tilted at the desired angle with respect to the optical axis of the optical microscope 50 or the optical axis of the ion beam when the specimen holder 100 is fitted to the specimen position adjustment mechanism 40. This makes it possible to adjust the incident angle of the ion beam with respect to the target on the specimen surface 4.

The specimen support 110 can rotate the specimen 2. For example, the specimen support 110 can rotate the specimen 2 around an axis that passes through the center of the surface on which the specimen 2 is placed. The specimen support 110 can rotate the specimen 2 around a normal that passes through the center of the specimen surface 4. It is possible to apply the ion beam to the target on the specimen surface 4 at various angles by causing the specimen support 110 to rotate the specimen 2.

The adjustment plate 120 is used to adjust the position of the specimen 2 using the optical microscope 50. The adjustment plate 120 is a plate-like member, for example. The adjustment plate 120 has an observation surface 122 that is observed using the optical microscope 50. The observation surface 122 is the surface of the adjustment plate 120 that faces the optical microscope 50. A marker 124 that serves as a mark used when positioning the specimen 2 is formed on the observation surface 122.

The marker 124 is formed at the end of the adjustment plate 120. The marker 124 perpendicularly and linearly extends from an edge 123 of the adjustment plate 120. Note that the edge 123 of the adjustment plate 120 is the edge of the adjustment plate 120 that comes in contact with (or is situated closest to) the specimen surface 4 when the adjustment plate 120 is supported by the adjustment plate support 130. The edge 123 of the adjustment plate 120 is formed by the surface of the adjustment plate 120 that comes in contact with (or is situated closest to) the specimen surface 4 and the observation surface 122. For example, the edge 123 of the adjustment plate 120 is placed parallel to the specimen surface 4. The adjustment plate 120 may be placed so that the entire edge 123 of the adjustment plate 120 comes in contact with the specimen surface 4.

The marker 124 may be provided by forming a recess in the adjustment plate 120, and may be provided by forming a protrusion on the adjustment plate 120, for example. The marker 124 may be formed by printing. The shape and the pattern of the marker 124 are not particularly limited. Although an example in which one marker 124 is provided is illustrated in the drawings, a plurality of markers 124 may be provided. The marker 124 may form a scale for measuring a length on the specimen surface 4.

The adjustment plate 120 is fitted to the adjustment plate support 130 so that the marker 124 indicates the position of the rotation center of the specimen support 110 (i.e., the rotation center of the specimen 2), for example. In this case, it is possible to adjust the rotation center of the specimen 2 to coincide with the application position of the ion beam, by positioning the specimen 2 so that the marker 124 is situated at the center of the field of view of the optical microscope 50. Note that the position indicated by the marker 124 is not limited to the rotation center of the specimen support 110. An arbitrary position on the specimen surface 4 may be indicated by the marker 124.

Adjustment plate securing members 126 are fitted to the opposite sides of the adjustment plate 120. The adjustment plate securing member 126 includes a permanent magnet, and is secured on the adjustment plate support 130 via a magnetic force, for example. Therefore, the adjustment plate 120 can be easily attached to, and removed from, the adjustment plate support 130.

The adjustment plate securing members 126 support the adjustment plate 120 so that the adjustment plate 120 is slidable in the longitudinal direction of the adjustment plate 120. Therefore, the adjustment plate 120 can be moved so that the distance from the specimen surface 4 can be changed. This makes it possible to bring the adjustment plate 120 into contact with the specimen 2 (or bring the adjustment plate 120 closer to the specimen 2) independently of the thickness of the specimen 2 and the convexities and concavities of the specimen surface 4 of the specimen 2. In the example illustrated in the drawings, the adjustment plate securing members 126 slide in the vertical direction relative to the specimen surface 4.

The adjustment plate support 130 supports the adjustment plate 120 through the adjustment plate securing members 126. The adjustment plate support 130 supports the adjustment plate 120 so that the adjustment plate 120 is tilted when the specimen 2 is tilted by the specimen support 110. Specifically, when the specimen tilt knob 112 is rotated, the adjustment plate support 130 rotates around the axis of the specimen tilt knob 112 together with the specimen support 110 so that the adjustment plate 120 is rotated (tilted) together with the specimen 2.

Figure 5:
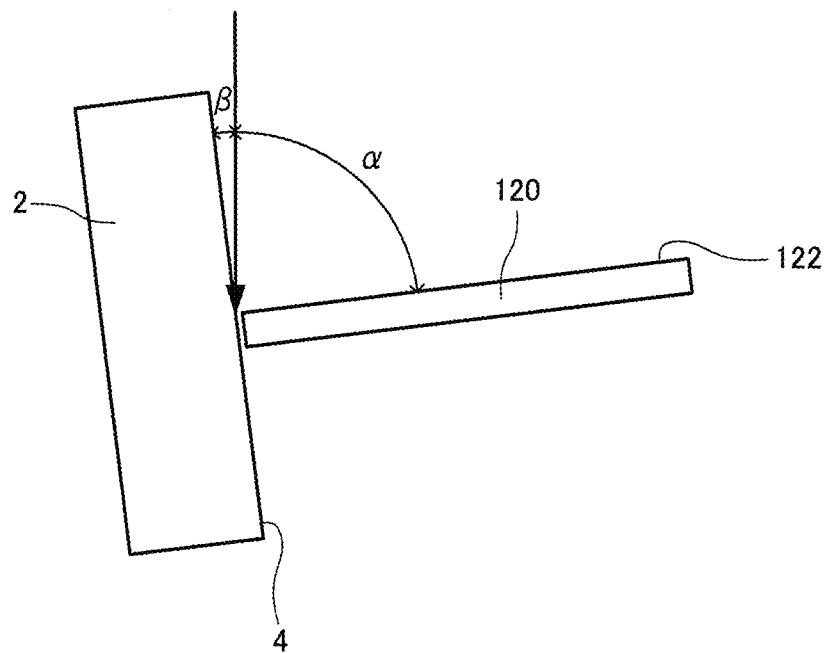
FIG. 5 is a view illustrating the positional relationship between a specimen and an adjustment plate.

FIG. 5 is a view illustrating the positional relationship between the specimen 2 and the adjustment plate 120. The arrow illustrated in FIG. 5 represents the optical axis of the optical microscope 50.

As illustrated in FIG. 5, the adjustment plate support 130 supports the adjustment plate 120 so that the angle alpha formed by the optical axis of the optical microscope 50 and the observation surface 122 of the adjustment plate 120 is larger than the angle beta formed by the optical axis of the optical microscope 50 and the specimen surface 4 (alpha>beta). Note that the angle alpha refers to the acute angle formed by the optical axis of the optical microscope 50 and the observation surface 122 of the adjustment plate 120. Likewise, the angle beta refers to the acute angle formed by the optical axis of the optical microscope 50 and the specimen surface 4. Note that the magnitude of the angle alpha and the magnitude of the angle beta can be changed by tilting the specimen 2 and the adjustment plate 120 using the specimen tilt knob 112.

In the example illustrated in the drawings, the angle formed by the observation surface 122 of the adjustment plate 120 and the specimen surface 4 of the specimen 2 is 90°. Since the adjustment plate 120 is tilted when the specimen 2 is tilted by the specimen support 110, the angle formed by the observation surface 122 of the adjustment plate 120 and the specimen surface 4 is 90° independently of the tilt angle of the specimen 2. Note that the angle formed by the observation surface 122 of the adjustment plate 120 and the specimen surface 4 is not limited to 90°. The angle formed by the observation surface 122 of the adjustment plate 120 and the specimen surface 4 may be set arbitrarily.

The support stage 140 supports the specimen support 110, the adjustment plate 120, the adjustment plate support 130, and the like. The support stage 140 is fitted to the specimen position adjustment mechanism 40.

2. Positioning Method

Figure 6:
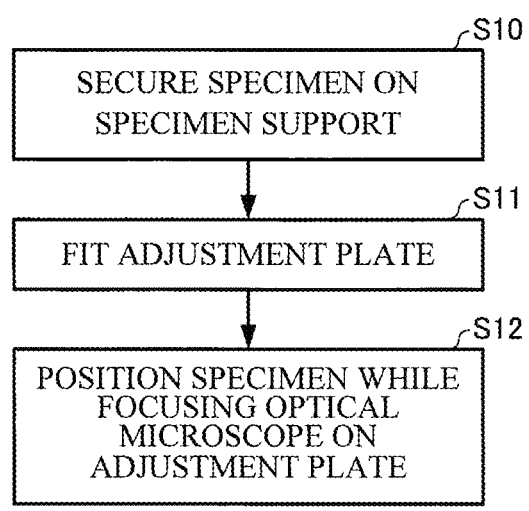
FIG. 6 is a flowchart illustrating an example of a positioning method according to one embodiment of the invention.

A specimen positioning method that utilizes the specimen holder and the specimen preparation device according to one embodiment of the invention is described below with reference to the drawings. FIG. 6 is a flowchart illustrating an example of the positioning method according to one embodiment of the invention.

As illustrated in FIG. 3, the specimen 2 is secured on the specimen support 110 of the specimen holder 100 (step S10).

The specimen 2 is secured on the specimen support 110 at a tilt angle that corresponds to the incident angle of the ion beam with respect to the specimen surface 4. For example, the specimen 2 is secured on the specimen support 110 so that the incident angle of the ion beam is close to 90° (i.e., an angle larger than 45° and smaller than 90°). In this case, the tilt angle of the specimen 2 is close to 90° (i.e., an angle larger than 45° and smaller than 90°).

The adjustment plate 120 is fitted to the adjustment plate support 130 (step S11).

The adjustment plate 120 is secured on the adjustment plate support 130 through the adjustment plate securing members 126. The adjustment plate 120 is placed so that the angle alpha formed by the optical axis of the optical microscope 50 and the observation surface 122 of the adjustment plate 120 is larger than the angle beta formed by the optical axis of the optical microscope 50 and the specimen surface 4 of the specimen 2, when the specimen holder 100 is fitted to the specimen position adjustment mechanism 40 (see FIG. 5). The adjustment plate 120 is slidable (see above), and the edge 123 of the adjustment plate 120 is brought into contact with (or brought closer to) the specimen 2 by sliding the adjustment plate 120.

In this case, the position at which the specimen 2 is secured on the specimen support 110 may be adjusted so that the target on the specimen surface 4 of the specimen 2 is situated at the position indicated by the marker 124 of the adjustment plate 120.

The specimen stage unloading mechanism 20 is then opened, and the specimen holder 100 is fitted to the specimen position adjustment mechanism 40 (see FIG. 1). Note that the specimen holder 100 may be fitted to the specimen position adjustment mechanism 40 in advance, and the step S10 and the step S11 may be performed while the specimen holder 100 is fitted to the specimen position adjustment mechanism 40.

The specimen 2 is then positioned while focusing the optical microscope 50 on the adjustment plate 120 (step S12).

Figure 7:
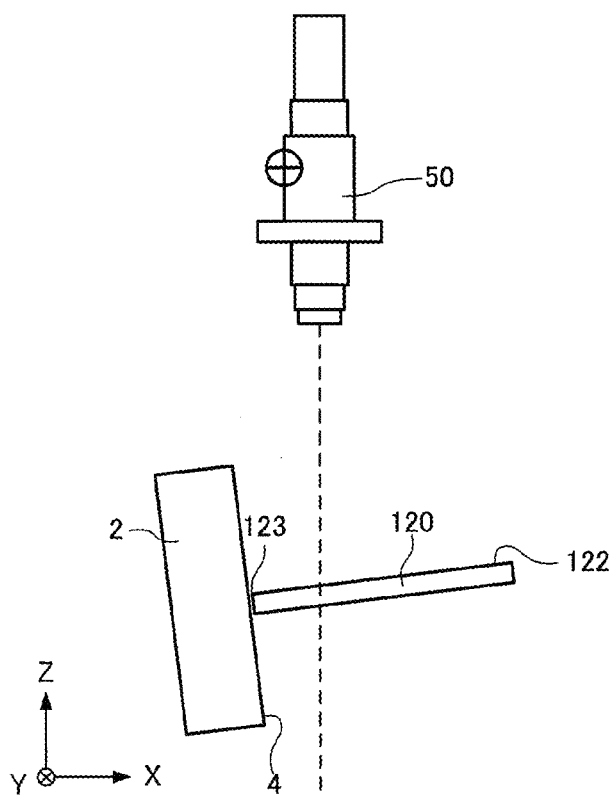
FIG. 7 is a view illustrating a step that positions a specimen.
Figure 8:
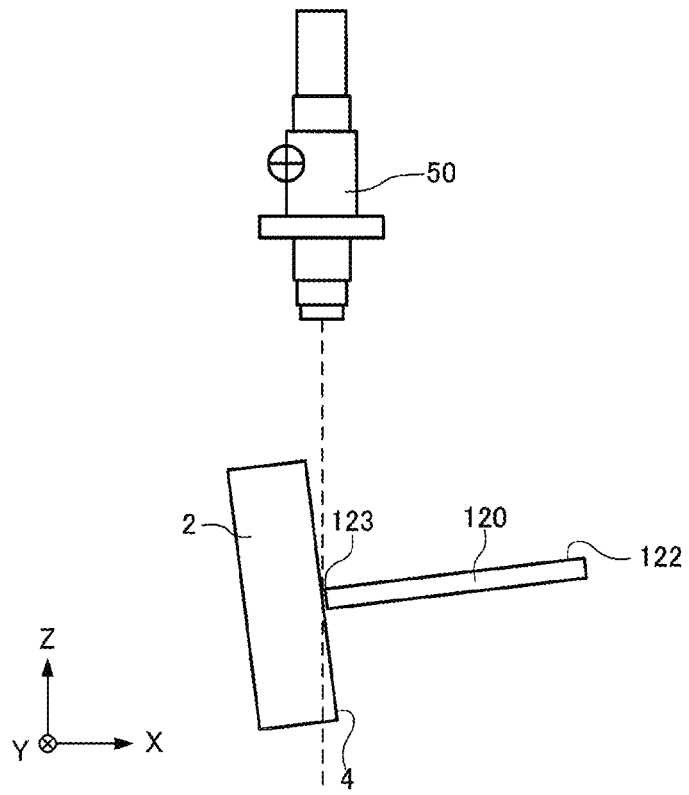
FIG. 8 is a view illustrating a step that positions a specimen.
Figure 9:
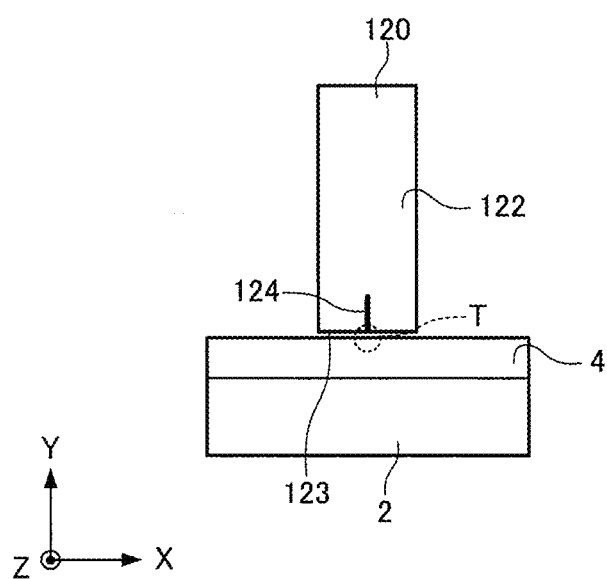
FIG. 9 is a view illustrating a step that positions a specimen.

FIGS. 7 to 9 are views illustrating the step (step S12) that focuses the optical microscope 50 on the adjustment plate 120, and positions the specimen 2. Note that FIG. 9 is a view schematically illustrating the state illustrated in FIG. 8 when viewed from the optical microscope (i.e., when viewed in the Z-axis direction). In FIGS. 7 to 9, the members of the specimen preparation device 1000 other than the optical microscope 50 and the adjustment plate 120 are omitted. The broken line illustrated in FIGS. 7 and 8 represents the optical axis of the optical microscope 50. The X-axis, the Y-axis, and the Z-axis are illustrated in FIGS. 7 to 9 as three axes that are orthogonal to each other. The Z-axis is an axis parallel to the optical axis of the optical microscope 50.

As illustrated in FIG. 7, the optical microscope 50 is focused on the observation surface 122 of the adjustment plate 120. Since the adjustment plate 120 has been secured in the step S11 so that the angle alpha formed by the optical axis of the optical microscope 50 and the observation surface 122 of the adjustment plate 120 is larger than the angle beta formed by the optical axis of the optical microscope 50 and the specimen surface 4, the optical microscope 50 can be easily focused on the observation surface 122 of the adjustment plate 120 as compared with the case of focusing the optical microscope 50 on the specimen surface 4.

The specimen 2 is then positioned using the adjustment plate 120 as a mark while observing the specimen 2 and the adjustment plate 120 using the optical microscope 50. As illustrated in FIGS. 8 and 9, the specimen holder 100 is moved using the specimen position adjustment mechanism 40 so that the position indicated by the marker 124 of the adjustment plate 120 coincides with the center T of the field of view of the optical microscope 50. The position of the specimen 2 indicated by the marker 124 is thus coincides with the center T of the field of view of the optical microscope 50. Therefore, the target on the specimen surface 4 is situated at the application position of the ion beam.

The specimen 2 can be positioned by performing the above steps.

The specimen preparation device 1000 processes the specimen 2 after the specimen 2 has been positioned.

Specifically, the adjustment plate 120 is removed from the adjustment plate support 130. After closing the specimen stage unloading mechanism 20, the processing chamber 1 is evacuated, and the ion beam generated by the ion source 10 is applied to the specimen surface 4 (see FIG. 2). The ion beam is thus applied to the target on the specimen surface 4 that has been positioned by the positioning step to process the specimen 2. Note that the ion beam can be applied to the target on the specimen surface 4 in various directions by rotating the specimen 2 using the specimen support 110.

The specimen 2 can be processed by performing the above steps to prepare an observation-analysis target specimen.

The specimen holder 100 and the specimen preparation device 1000 have the following features, for example.

The specimen holder 100 is configured so that the specimen support 110 supports the specimen 2 so that the specimen 2 can be tilted relative to the optical axis of the optical microscope 50, and the adjustment plate support 130 supports the adjustment plate 120 so that the angle formed by the optical axis of the optical microscope 50 and the observation surface 122 of the adjustment plate 120 is larger than the angle formed by the optical axis of the optical microscope 50 and the specimen surface 4 of the specimen 2. Therefore, the optical microscope 50 can be focused on the observation surface 122 of the adjustment plate 120 over a wide range as compared with the specimen surface 4. It is possible to easily and accurately position the specimen 2 by positioning the specimen 2 while focusing the optical microscope 50 on the adjustment plate 120.

Since the specimen holder 100 is configured so that the specimen 2 can be positioned while focusing the optical microscope 50 on the adjustment plate 120, the specimen 2 can be positioned while the specimen surface 4 is tilted. For example, when the specimen is tilted after the specimen has been positioned while the specimen surface is perpendicular to the optical axis of the optical microscope, the position of the target may be shifted depending on the accuracy of the tilt mechanism. Since the specimen holder 100 is configured so that the specimen 2 can be positioned while the specimen surface 4 is tilted, it is possible to accurately position the specimen 2 as compared with the case where the specimen is tilted after the specimen has been positioned while the specimen surface is perpendicular to the optical axis of the optical microscope, for example.

According to the specimen holder 100, the application position of the ion beam in the specimen preparation device 1000 can be clearly indicated using the adjustment plate 120. Moreover, the processing position on the specimen surface 4 can be determined by adjusting the position at which the specimen 2 is secured on the specimen support 110 using the adjustment plate 120.

The specimen holder 100 is configured so that the marker 124 that serves as a mark used when positioning the specimen 2 is formed on the observation surface 122 of the adjustment plate 120. Therefore, the specimen 2 can be positioned using the optical microscope 50 utilizing the marker 124 as a mark, and it is possible to more accurately position the specimen 2.

The specimen holder 100 is configured so that the adjustment plate 120 can be moved so that the distance from the specimen surface 4 can be changed. This makes it possible to bring the adjustment plate 120 into contact with the specimen 2 (or bring the adjustment plate 120 closer to the specimen 2) independently of the thickness of the specimen 2 and the convexities and concavities of the specimen surface 4 of the specimen 2. Therefore, the adjustment plate 120 (marker 124) can be brought into contact with the target on the specimen surface 4 (or brought closer to the target on the specimen surface 4), and it is possible to more accurately position the specimen 2, for example.

The specimen holder 100 is configured so that the adjustment plate support 130 supports the adjustment plate 120 so that the adjustment plate 120 is tilted when the specimen 2 is tilted by the specimen support 110. Therefore, the angle formed by the specimen surface 4 of the specimen 2 and the observation surface 122 of the adjustment plate 120 can be set to be constant independently of the tilt angle of the specimen 2.

The specimen holder 100 is configured so that the angle formed by the specimen surface 4 and the observation surface 122 of the adjustment plate 120 is 90°. Therefore, the angle formed by the observation surface 122 of the adjustment plate 120 and the optical axis of the optical microscope 50 can be set to be close to 90° when processing the specimen surface 4 by applying the ion beam to the specimen surface 4 at an incident angle close to 90°. Therefore, the optical microscope 50 can be focused on the observation surface 122 of the adjustment plate 120 over a wide range. This makes it possible to easily position the specimen 2 using the optical microscope 50.

The specimen preparation device 1000 includes the specimen holder 100. Therefore, it is possible to easily and accurately position the specimen 2.

The specimen preparation device 1000 includes the ion source 10, and applies the ion beam generated by the ion source 10 to the specimen 2 to process the specimen 2. Therefore, it is possible to easily and accurately process the desired position of the specimen 2 using the specimen preparation device 1000.

The positioning method according to one embodiment of the invention has the following features, for example.

Since the positioning method according to one embodiment of the invention places the adjustment plate 120 relative to the specimen 2 that is supported to enable the specimen surface 4 to be tilted relative to the optical axis of the optical microscope 50, so that the angle alpha formed by the optical axis of the optical microscope 50 and the observation surface 122 of the adjustment plate 120 is larger than the angle beta formed by the optical axis of the optical microscope 50 and the specimen surface 4, the optical microscope 50 can be focused on the observation surface 122 of the adjustment plate 120 over a wide range as compared with the specimen surface 4. Therefore, it is possible to easily and accurately position the specimen 2, by positioning the specimen 2 while focusing the optical microscope 50 on the adjustment plate 120.

Since the positioning method according to one embodiment of the invention positions the specimen 2 while focusing the optical microscope 50 on the adjustment plate 120, the specimen 2 can be positioned while the specimen surface 4 is tilted. This makes it possible to more accurately position the specimen 2, as compared with the case where the specimen is tilted after the specimen has been positioned while the specimen surface 4 is perpendicular to the optical axis of the optical microscope 50, for example.

Since the marker 124 which serves as a mark used when positioning the specimen 2 is formed on the observation surface 122 of the adjustment plate 120, the positioning method according to one embodiment of the invention can more accurately position the specimen 2.

Figure 10:
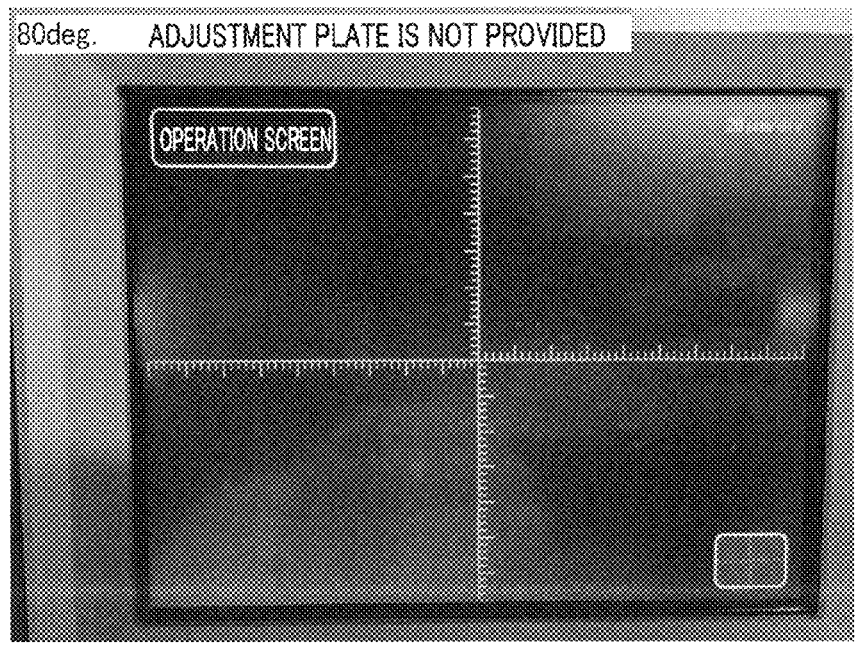
FIG. 10 illustrates an image that represents an observation result obtained using an optical microscope, when a specimen is tilted by 80°.

FIG. 10 illustrates an image that represents the observation result obtained using the optical microscope when the specimen is tilted by 80°. Specifically, the angle formed by the optical axis of the optical microscope and the specimen surface is 10°.

As illustrated in FIG. 10, when the specimen is tilted by 80°, the focus range of the optical microscope is narrow with respect to the tilt of the specimen, and the specimen surface cannot be observed under the optical microscope.

Figure 11:
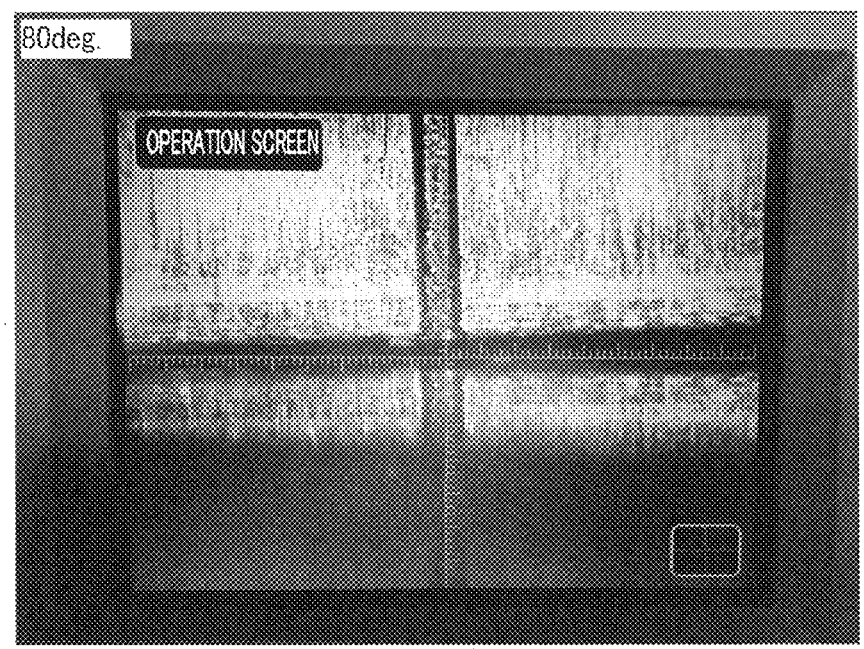
FIG. 11 illustrates an image that represents an observation result obtained using an optical microscope, when a specimen is tilted while an adjustment plate is provided.
Figure 12:
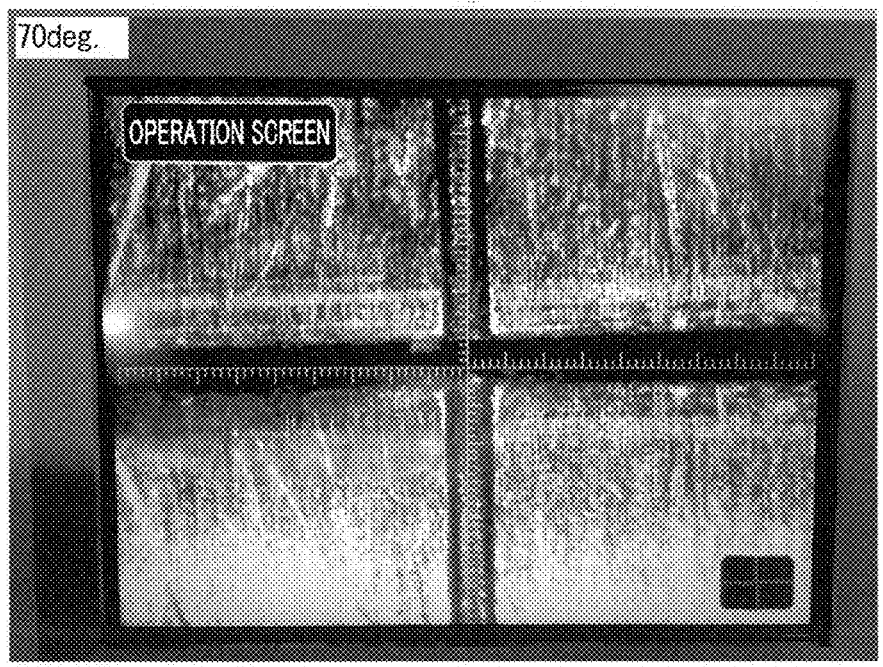
FIG. 12 illustrates an image that represents an observation result obtained using an optical microscope, when a specimen is tilted while an adjustment plate is provided.
Figure 13:
FIG. 13 illustrates an image that represents an observation result obtained using an optical microscope, when a specimen is tilted while an adjustment plate is provided.
Figure 14:
FIG. 14 illustrates an image that represents an observation result obtained using an optical microscope when a specimen is tilted by 45°.

FIGS. 11 to 13 illustrate an image that represents the observation result obtained using the optical microscope, when the specimen is tilted while the adjustment plate is provided. Note that FIG. 11 illustrates the case where the specimen is tilted by 80°; FIG. 12 illustrates the case where the specimen is tilted by 70°, and FIG. 13 illustrates the case where the specimen is tilted by 45°. In FIGS. 11 to 13, the adjustment plate is provided so that the angle formed by the observation surface of the adjustment plate and the specimen surface is 90°. FIG. 14 illustrates an image that represents the observation result obtained using the optical microscope when the specimen is tilted by 45°. Specifically, FIG. 14 illustrates an image that represents the observation result when the adjustment plate is removed from the state illustrated in FIG. 13.

As illustrated in FIGS. 11 to 13, the adjustment plate can be clearly observed using the optical microscope, when the specimen is tilted by 80°, 70°, or 45°. Therefore, the specimen surface can be easily positioned at the center of the field of view of the optical microscope. In FIGS. 11 to 13, the upper half of the operation screen corresponds to the adjustment plate, and the lower half of the operation screen corresponds to the specimen. In FIGS. 11 and 12, the observation surface of the adjustment plate is reflected on the specimen surface.

It was thus confirmed that it is possible to easily position the specimen even when the specimen surface is tilted, by providing the adjustment plate.

3. Modifications

Modification of the specimen holder and the specimen preparation device according to one embodiment of the invention are described below.

(1) First Modification

Figure 15:
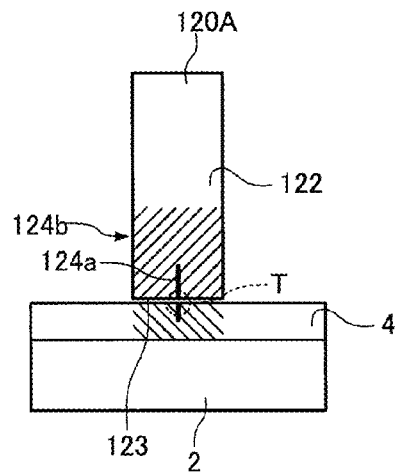
FIG. 15 is a view schematically illustrating an adjustment plate of a specimen holder according to a first modification of one embodiment of the invention.

A first modification is described below. FIG. 15 is a view schematically illustrating an adjustment plate 120A of the specimen holder according to the first modification. Note that FIG. 15 is a view schematically illustrating a state in which the adjustment plate 120A is observed under the optical microscope 50, and corresponds to FIG. 9.

The members of the adjustment plate according to the first modification that have the same functions as those of the adjustment plate 120 are indicated by the same reference signs (symbols), and description thereof is omitted. The configuration of the specimen holder and the specimen preparation device according to the first modification other than the adjustment plate is the same as that of the specimen holder 100 and the specimen preparation device 1000, and description thereof is omitted.

In the above embodiments the marker 124 that perpendicularly and linearly extends from the edge 123 is formed on the observation surface 122 of the adjustment plate 120 (see FIG. 9).

As illustrated in FIG. 15, the marker 124 (hereinafter may be referred to as "first marker 124a") that perpendicularly and linearly extends from the edge 123 and a second marker 124b are formed on the observation surface 122 of the adjustment plate 120A according to the first modification.

The second marker 124b is formed so that the boundary between the adjustment plate 120A and the specimen 2 can be clearly determined even when the observation surface 122 of the adjustment plate 120A is reflected on the specimen surface 4, when the specimen 2 is positioned using the optical microscope 50.

The second marker 124b forms a pattern that includes a plurality of straight lines that extend from the edge 123 of the adjustment plate 120A in a diagonal direction (i.e., a direction that is tilted relative to the normal to the edge 123). Therefore, the boundary between the adjustment plate 120A and the specimen 2 can be clearly determined even when the observation surface 122 of the adjustment plate 120A is reflected on the specimen surface 4 (see FIG. 9).

For example, in the case where only the first marker 124a is formed on the observation surface 122 of the adjustment plate 120A, the first marker 124a formed on the observation surface 122 and the first marker 124a reflected on the specimen surface 4 form a single straight line when the observation surface 122 of the adjustment plate 120A is reflected on the specimen surface 4, and it is difficult to determine the boundary between the adjustment plate 120A and the specimen 2.

Note that the pattern of the second marker 124b is not limited to the example illustrated in FIG. 9. It suffices that the second marker 124b include a part that extends from the edge 123 of the adjustment plate 120A in a diagonal direction (i.e., a direction that is tilted relative to the normal to the edge 123).

FIGS. 16 to 19 are views illustrating a modification of the pattern of the second marker 124b.

Figure 16:
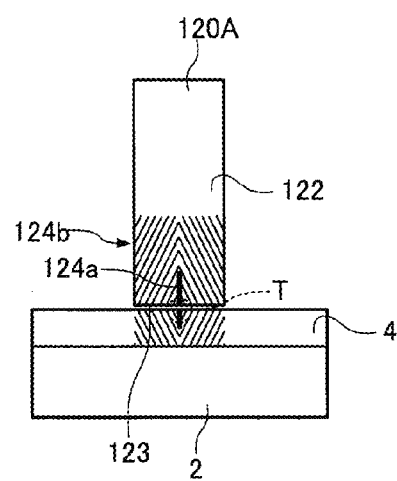
FIG. 16 is a view illustrating a modification of the pattern of a second marker.
Figure 17:
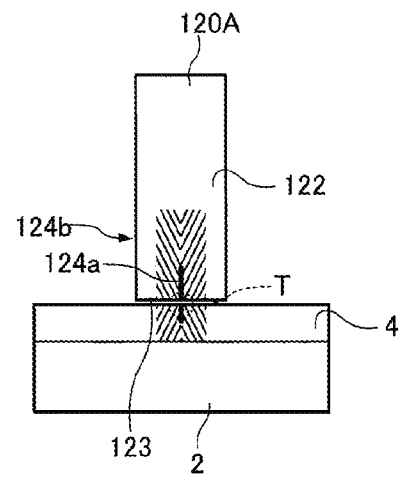
FIG. 17 is a view illustrating a modification of the pattern of a second marker.
Figure 18:
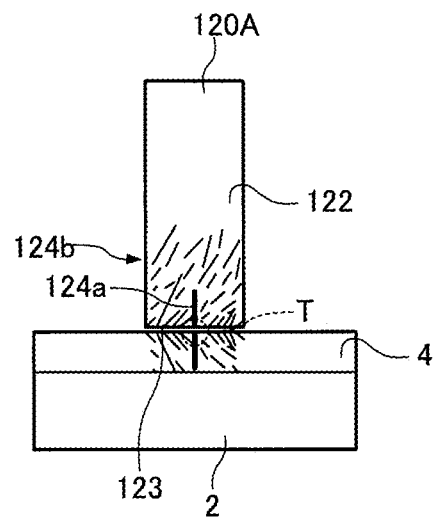
FIG. 18 is a view illustrating a modification of the pattern of a second marker.
Figure 19:
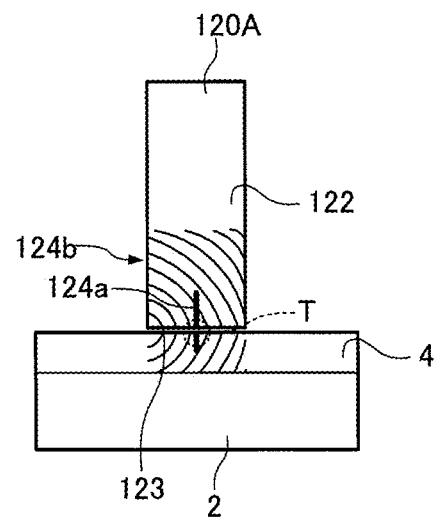
FIG. 19 is a view illustrating a modification of the pattern of a second marker.

As illustrated in FIG. 16, the second marker 124b may form a pattern that is line-symmetrical with respect to an axis that extends along the first marker 124a. As illustrated in FIG. 17, the second marker 124b may be formed in part of the end of the adjustment plate 120A that is on the side of the edge 123. As illustrated in FIG. 18, the second marker 124b may form an irregular pattern (e.g., a pattern that is formed by hairline finish). As illustrated in FIG. 19, the second marker 124b may form a pattern formed by curves.

Note that only the second marker 124b may be formed on the observation surface 122 of the adjustment plate 120A without forming the first marker 124a.

The second marker 124b may be formed by printing, for example. When the second marker 124b forms an irregular pattern (see FIG. 18), for example, the second marker 124b may be formed by hairline finish.

In the specimen holder according to the first modification, the second marker 124b has a part that extends from the edge 123 of the adjustment plate 120A in a diagonal direction. Therefore, the boundary between the adjustment plate 120A and the specimen 2 can be clearly determined even when the observation surface 122 of the adjustment plate 120A is reflected on the specimen surface 4, when the specimen 2 is positioned using the optical microscope 50. This makes it possible to easily and accurately position the specimen 2 using the optical microscope 50.

(2) Second Modification

Figure 20:
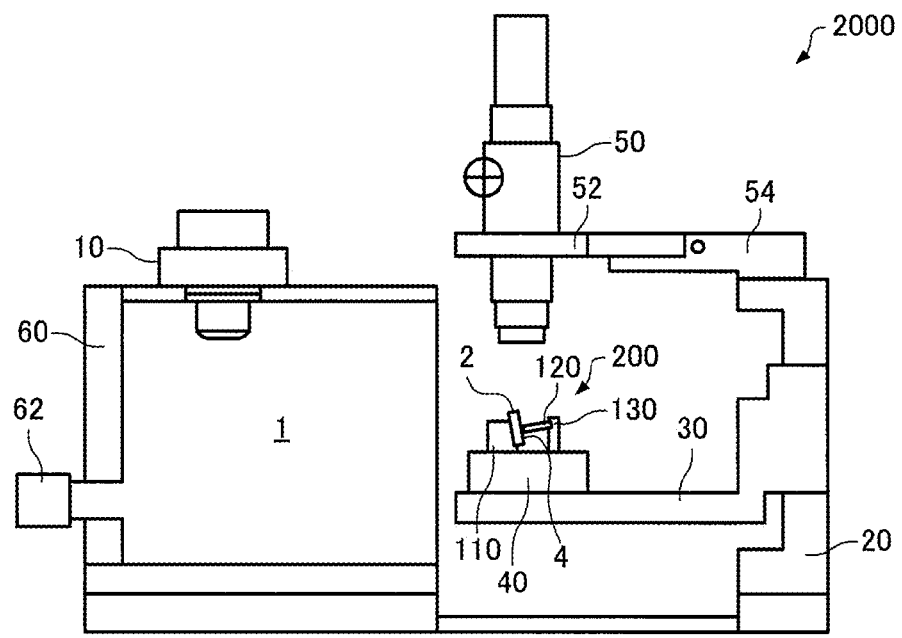
FIG. 20 is a view schematically illustrating a specimen holder and a specimen preparation device according to a second modification of one embodiment of the invention.
Figure 21:
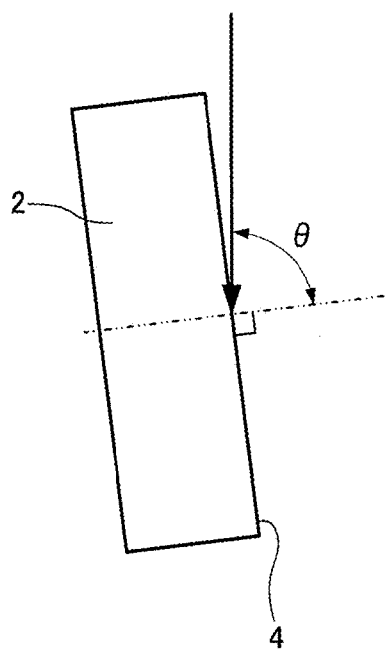
FIG. 21 is a view schematically illustrating a specimen when processing the specimen by applying an ion beam to a specimen surface at an incident angle close to 90°.
Figure 22A:
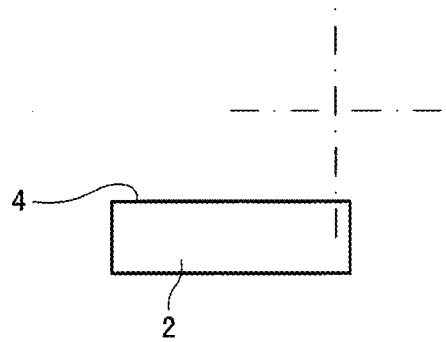
FIGS. 22A to 22D are views illustrating an example of a known specimen positioning method.
Figure 22B:
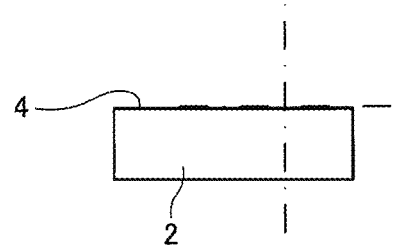
Figure 22C:
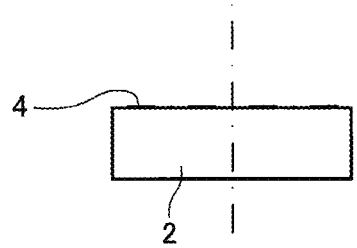
Figure 22D:
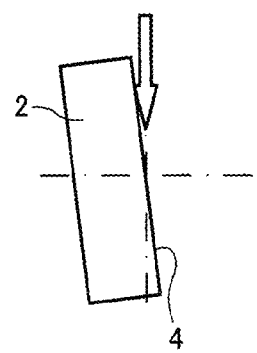

A specimen holder and a specimen preparation device according to a second modification are described below with reference to FIG. 20. FIG. 20 is a view schematically illustrating a specimen holder 200 and a specimen preparation device 2000 according to the second modification. Note that the specimen holder 200 is illustrated in FIG. 20 in a simplified manner for convenience of illustration.

The members of the specimen holder 200 and the specimen preparation device 2000 according to the second modification that have the same functions as those of the specimen holder 100 and the specimen preparation device 1000 are indicated by the same reference signs (symbols), and description thereof is omitted.

The specimen holder 100 is configured so that the specimen support 110 and the adjustment plate support 130 are integrally provided in such a way that the adjustment plate 120 is tilted when the specimen 2 is tilted by the specimen support 110.

As illustrated in FIG. 20, the specimen holder 200 has a configuration in which the specimen support 110 and the adjustment plate support 130 are provided independently of each other.

The specimen holder 200 has a configuration in which the specimen support 110 that supports the specimen 2 and the adjustment plate support 130 that supports the adjustment plate 120 are separately provided on the specimen position adjustment mechanism 40. Therefore, the adjustment plate 120 is not tilted when the specimen 2 (specimen surface 4) is tilted by the specimen support 110, for example.

Note that the position of the adjustment plate support 130 is not particularly limited. For example, the adjustment plate support 130 may be provided on the specimen stage 30 (not illustrated in the drawings). Alternatively, the specimen support 110 and the adjustment plate support 130 may respectively be provided to different position adjustment mechanisms so that the specimen 2 and the adjustment plate 120 can be moved independently of each other, for example.

The specimen holder 200 according to the second modification can achieve the same advantageous effects as those achieved by the specimen holder 100.

Since the specimen preparation device 2000 according to the second modification includes the specimen holder 200, the specimen preparation device 2000 can achieve the same advantageous effects as those achieved by the specimen preparation device 1000.

(3) Third Modification

Although the above embodiments have been described taking an example in which the specimen preparation device 1000 is an ion beam device that applies the ion beam to the specimen 2 to process the specimen 2, the specimen holder according to the invention can be applied to various devices that observe or position a specimen using an optical microscope.

Note that the above embodiments and modifications are merely examples, and the invention is not limited to the above embodiments and modifications. For example, the above embodiments and modifications may be appropriately combined.

The invention includes various other configurations substantially the same as the configurations described in connection with the above embodiments (e.g., a configuration having the same function, method, and results, or a configuration having the same objective and effects). The invention also includes a configuration in which an unsubstantial element described in connection with the above embodiments is replaced by another element. The invention also includes a configuration having the same effects as those of the configurations described in connection with the above embodiments, or a configuration capable of achieving the same objective as that of the configurations described in connection with the above embodiments. The invention further includes a configuration in which a known technique is added to the configurations described in connection with the above embodiments.

Although only some embodiments of the invention have been described in detail above, those skilled in the art would readily appreciate that many modifications are possible in the embodiments without materially departing from the novel teachings and advantages of the invention. Accordingly, all such modifications are intended to be included within the scope of the invention.

What is claimed is:

1. A specimen holder that is used for an optical microscope, comprising:
    a specimen support that supports a specimen to enable the specimen to tilt relative to an optical axis of the optical microscope;
    an adjustment plate that has an observation surface for making observations using the optical microscope; and
    an adjustment plate support that supports the adjustment plate so that an angle formed by the optical axis and the observation surface is larger than an angle formed by the optical axis and a specimen surface of the specimen.

2. The specimen holder as defined in claim 1,
    wherein a marker that serves as a mark used when positioning the specimen is formed on the observation surface.

3. The specimen holder as defined in claim 2,
    wherein the adjustment plate is movable so that a distance from the specimen surface can be changed.

4. The specimen holder as defined in claim 2,
    wherein the marker includes a part that extends from an edge of the adjustment plate in a diagonal direction.

5. The specimen holder as defined in claim 1,
    wherein the adjustment plate support supports the adjustment plate, so that the adjustment plate tilts when the specimen is tilted by the specimen support.

6. The specimen holder as defined in claim 1,
    wherein an angle formed by the specimen surface and the observation surface is 90°.

7. A specimen preparation device comprising:
    the specimen holder as defined in claim 1.

8. The specimen preparation device as defined in claim 7, further comprising:
    an ion source that generates an ion beam,
    the specimen preparation device applying the ion beam to the specimen to process the specimen.

9. A positioning method that positions a specimen using an optical microscope, the positioning method comprising:
    placing an adjustment plate relative to a specimen that is supported to enable a specimen surface to tilt relative to an optical axis of the optical microscope, so that an angle formed by the optical axis and an observation surface of the adjustment plate is larger than an angle formed by the optical axis and the specimen surface; and
    positioning the specimen while focusing the optical microscope on the adjustment plate.

10. The positioning method as defined in claim 9,
    wherein a marker that serves as a mark used when positioning the specimen is formed on the observation surface.

* * * * *